US010688276B2

(12) United States Patent
Gianotti et al.

(10) Patent No.: US 10,688,276 B2
(45) Date of Patent: Jun. 23, 2020

(54) LENGTH-ADJUSTABLE CATHETER AND METHOD THAT EMPLOYS A LENGTH-ADJUSTABLE CATHETER TO TREAT VASCULAR PATHOLOGIES

(71) Applicant: CTI Vascular AG, Neuhausen (CH)

(72) Inventors: Marc Gianotti, Wiesendangen (CH); Michael Jetter, Thayngen (CH); Martin Rickert, Rottweil (DE); Dragana Gajic, Schaffhausen (CH); Sabina Silva, Diessenhofen (CH); Andreas Bodmer, Windisch (CH); Valentin Nickel, Singen-Schlatt (DE); Ulf Fritz, Tengen (DE)

(73) Assignee: CTI Vascular AG, Neuhausen (CH)

( * ) Notice: Subject to any disclaimer, the term of this patent is extended or adjusted under 35 U.S.C. 154(b) by 186 days.

(21) Appl. No.: 15/502,729

(22) PCT Filed: Aug. 26, 2015

(86) PCT No.: PCT/IB2015/001981
§ 371 (c)(1),
(2) Date: Feb. 8, 2017

(87) PCT Pub. No.: WO2017/033039
PCT Pub. Date: Mar. 2, 2017

(65) Prior Publication Data
US 2018/0154110 A1    Jun. 7, 2018

(51) Int. Cl.
A61M 25/00    (2006.01)
A61M 25/10    (2013.01)
(Continued)

(52) U.S. Cl.
CPC ........ A61M 25/0043 (2013.01); A61M 25/01 (2013.01); A61M 25/0108 (2013.01);
(Continued)

(58) Field of Classification Search
CPC .. A61M 2025/0175; A61M 2205/0216; A61M 2205/582; A61M 2205/583;
(Continued)

(56) References Cited

U.S. PATENT DOCUMENTS 5,466,222 A * 11/1995 Ressemann ......... A61M 25/104
                                                      604/103.09
5,497,782 A *  3/1996 Fugoso ............. A61M 25/0169
                                                            600/585

(Continued)

Primary Examiner — Kathleen S Holwerda
Assistant Examiner — Brooke LaBranche
(74) Attorney, Agent, or Firm — Olympic Patent Works PLLC

(57) ABSTRACT

The current document is directed to length-adjustable catheters and methods that employ length-adjustable catheters to treat malformations, constrictions, obstructions, lesions, and blockages within patients' blood vessels. The length of the shaft of a length-adjustable catheter, to which the current application is directed, can be adjusted over a range of lengths prior to and during medical procedures. In many implementations, length adjustment is accompanied by indications, to the medical provider, of the extent of a length adjustment. The indications may include one or more of visual markings, haptic feedback, radio-opaque markings, and/or other types of indications. In many implementations, the variable-length mechanism of the length-adjustable catheter is mechanically lockable following length adjustment.

1 Claim, 15 Drawing Sheets

(51) Int. Cl.
*A61M 25/01* (2006.01)
*A61M 25/09* (2006.01)

(52) U.S. Cl.
CPC .......... *A61M 25/09* (2013.01); *A61M 25/104* (2013.01); *A61M 2025/0079* (2013.01); *A61M 2025/0175* (2013.01); *A61M 2205/0216* (2013.01); *A61M 2205/582* (2013.01); *A61M 2205/583* (2013.01)

(58) Field of Classification Search
CPC .......... A61M 25/0043; A61M 25/0108; A61M 25/09; A61M 25/104
See application file for complete search history.

(56) References Cited

U.S. PATENT DOCUMENTS

| | | | |
|---|---|---|---|
| 5,797,782 A | | 8/1998 | Blecker et al. |
| 5,846,259 A | * | 12/1998 | Berthiaume .......... A61M 25/00 606/192 |
| 5,968,012 A | * | 10/1999 | Ren .................... A61M 25/104 604/103 |
| 2003/0105451 A1 | * | 6/2003 | Westlund .......... A61M 25/0021 604/532 |
| 2014/0171914 A1 | * | 6/2014 | Rowe .................... A61M 25/02 604/510 |
| 2017/0281915 A1 | * | 10/2017 | Jalgaonkar ......... A61M 25/1011 |

\* cited by examiner

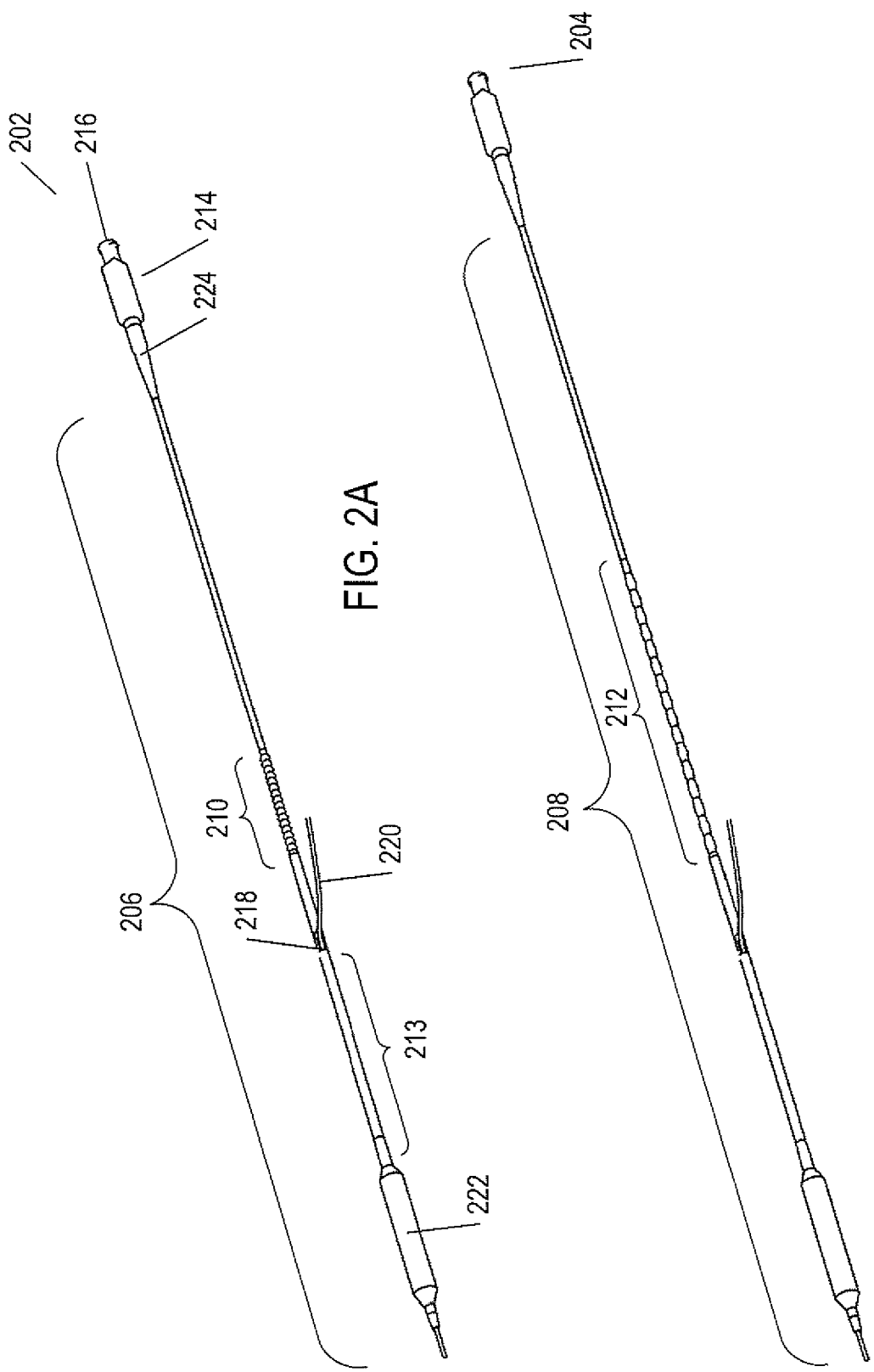

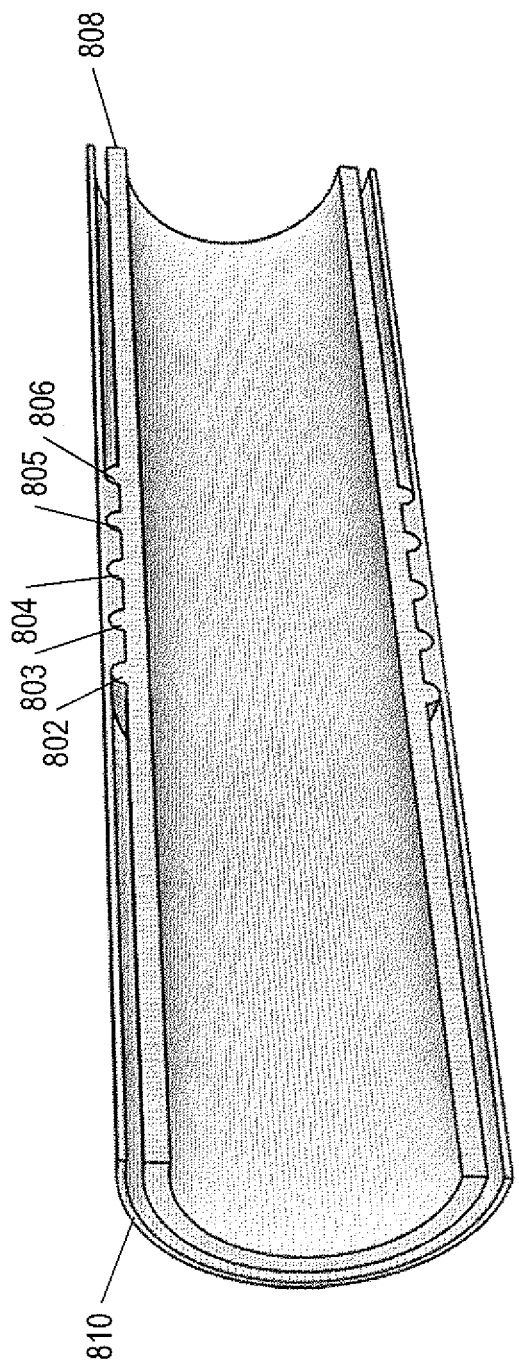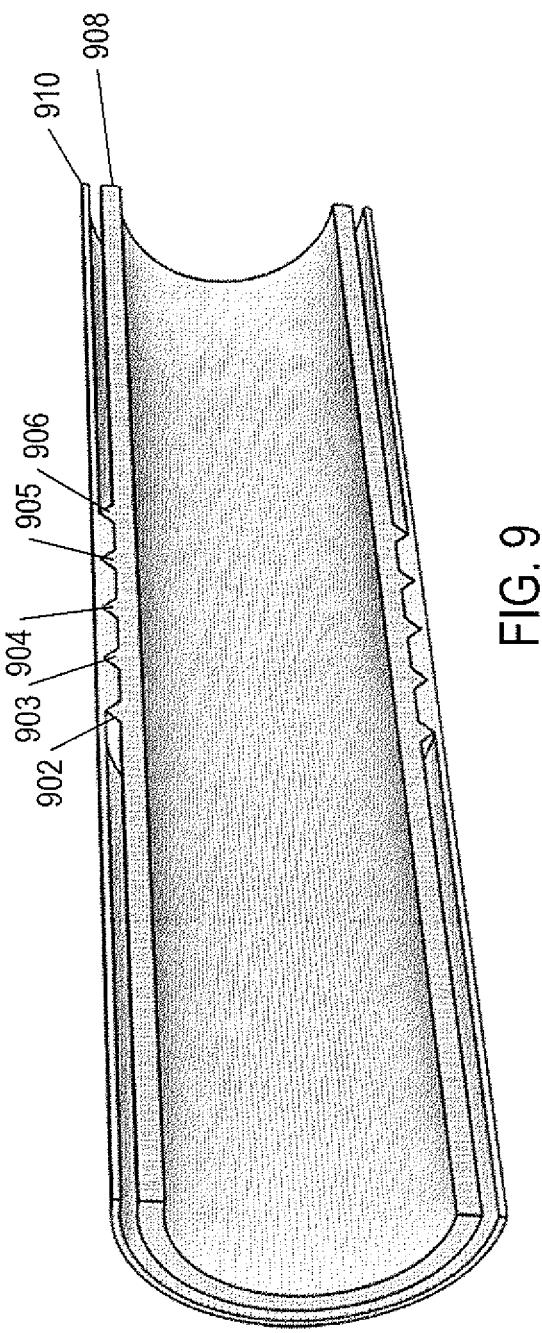

LENGTH-ADJUSTABLE CATHETER AND METHOD THAT EMPLOYS A LENGTH-ADJUSTABLE CATHETER TO TREAT VASCULAR PATHOLOGIES

TECHNICAL FIELD

The current document is directed to catheters used to treat vascular pathologies and, in particular, to catheters with variable shaft lengths that are used for treating a variety of different vascular conditions.

BACKGROUND

Angioplasty balloon catheters have been developed to treat a variety of different manifestations of vascular disease within patients' veins and arteries that, when not treated, often lead to increasingly serious health conditions and complications, including ischemia, heart attacks, embolisms, and strokes. An angioplasty balloon catheter is generally inserted, along a previously inserted guide wire, into a patient's blood vessel at a variety of different blood-vessel access points, including the femoral, subclavian, radial, and brachial arteries. The catheter is advanced along the guide wire in order to position the inflatable portion of the angioplasty balloon catheter in or near a target region of the blood vessel. The balloon is then inflated in order to mechanically dilate and displace a blockage, lesion, or other problem within the target region. Currently available angioplasty balloon catheters have fixed shaft lengths. As a result, a treatment provider generally selects a balloon angioplasty catheter of appropriate length in order to access a particular treatment site from a particular access point. However, in many procedures, a vessel is blocked at more than one point. In many cases, the treatment provider therefore needs to employ two or more angioplasty balloon catheters of two or more different lengths in order to reach and ameliorate the two or more blockages from the particular access point. Because angioplasty-balloon-catheter-based procedures involve prior insertion of the guide wire, insertion and removal of multiple, different-length angioplasty balloon catheters may result in a variety of cascading complexities and problems, including a need to remove and reinsert different-length guide wires, complexities associated with maintaining sterile protocols across multiple sub-procedures, increased procedure times, and potential for additional complications arising from additional procedural steps, including risk of vessel damage and unintentional vessel-wall penetration. Designers, developers, and treatment providers therefore continue to seek new and improved treatment equipment and associated methods for treating blood-vessel malformations, constrictions, obstructions, lesions, and blockages.

SUMMARY

The current document is directed to length-adjustable catheters and methods that employ length-adjustable catheters to treat malformations, constrictions, obstructions, lesions, and blockages within patients' blood vessels. The length of the shaft of a length-adjustable catheter, to which the current application is directed, can be adjusted over a range of lengths prior to and during medical procedures. In many implementations, length adjustment is accompanied by relative-position indications, to the medical provider, of the extent of a length adjustment. The indications may include one or more of visual markings, haptic feedback, radio-opaque markings, and/or other types of indications. In many implementations, the variable-length mechanism of the length-adjustable catheter is mechanically lockable following length adjustment.

BRIEF DESCRIPTION OF THE DRAWINGS

FIGS. 2A-B illustrate a second implementation of the length-adjustable angioplasty balloon catheter.

FIGS. 6-11 show a variety of different implementations of dual-lumen and single-lumen shaft-tube engagement configurations and locking mechanisms.

DETAILED DESCRIPTION

The current document is directed to a variety of different implementations of catheters with length-adjustable shafts that are used to treat vascular pathologies. The length-adjustable catheters facilitate both treatments of single target sites within blood vessels as well as procedures that involve treatment of multiple target sites. Because the shaft length of a length-adjustable catheter can be changed during a medical procedure, after the catheter has been initially inserted into a patient's blood vessel, the length-adjustable catheter provides for adjustment of initial non-optimal placements, changes to which might otherwise involve removal of an initially inserted first catheter and reinsertion of a second catheter with a different length. The catheter significantly simplifies treatments of multiple target sites within a blood vessel, since the length of the length-adjustable catheter can be changed, during a procedure, following treatment of a first target site, in order to reposition the catheter to treat a second target site. Length-adjustable catheters may also reduce needed equipment inventories, since fewer different length-adjustable catheters are needed to span the potential range of usable lengths needed for accessing variably positioned treatment sites encountered in human anatomy. In the following discussion, examples of length-adjustable angioplasty balloon catheter are illustrated and described. Angioplasty balloon catheters are commonly employed in a variety of medical treatments. The length-adjustability discussed with reference to the various implementations of angioplasty balloon catheters can be applied to, and incorporated within, other types of catheters used for diagnostic and therapeutic procedures.

Figure 1A:
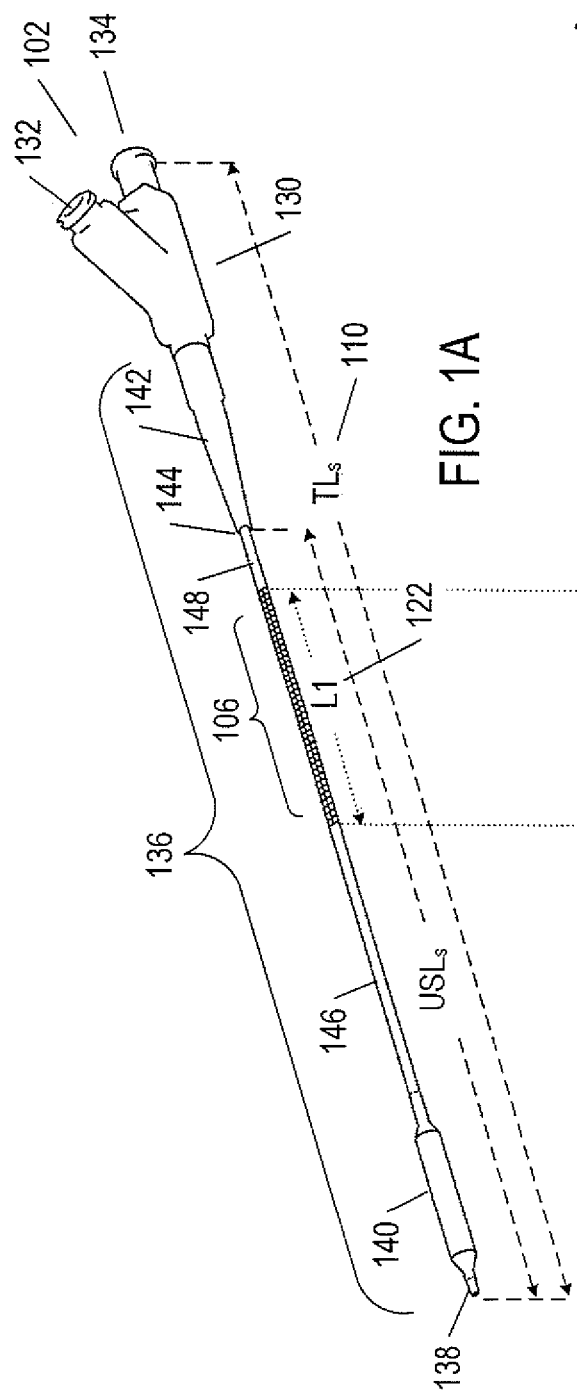
FIGS. 1A-B illustrate a first implementation of a length-adjustable angioplasty balloon catheter.
Figure 1B:
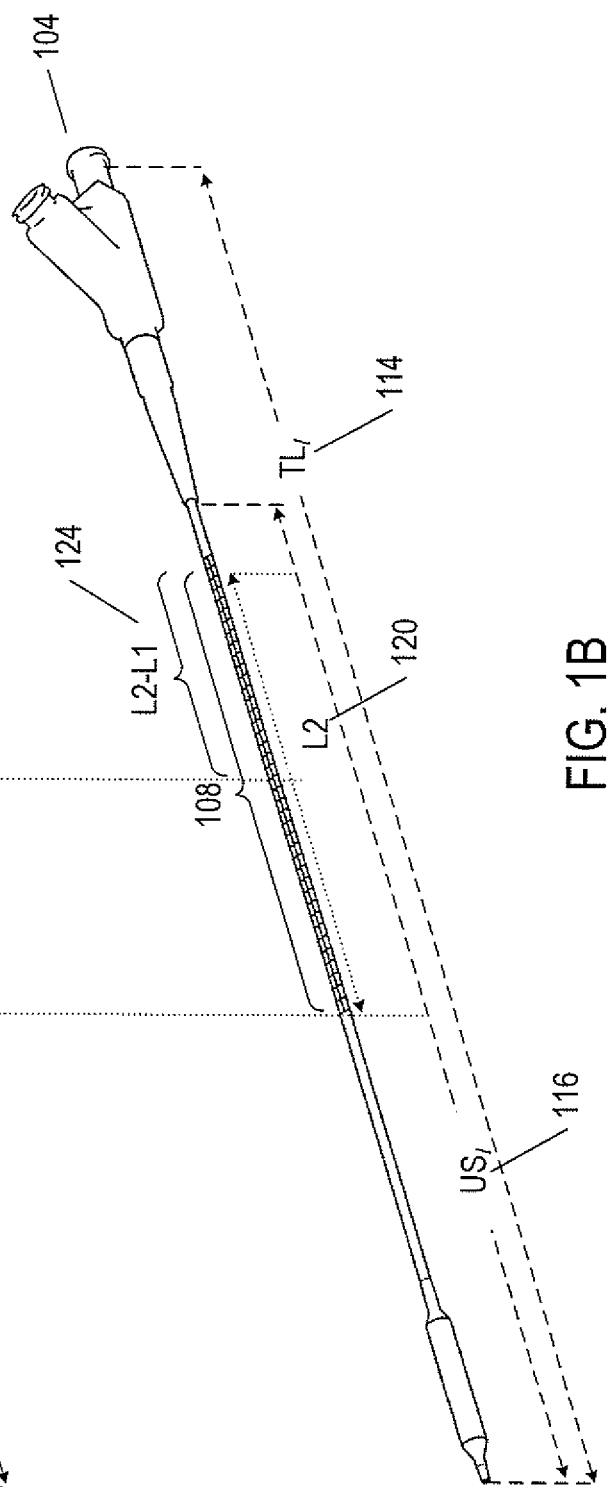

FIGS. 1A-B illustrate a first implementation of a length-adjustable angioplasty balloon catheter. FIG. 1A shows the length-adjustable angioplasty balloon catheter 102 in a fully contracted configuration and FIG. 1B shows the length-adjustable angioplasty balloon catheter 104 in a fully extended configuration. The range of lengths that can be adopted by the length-adjustable angioplasty balloon catheter arises from extension and contraction of a variable-length portion of the length-adjustable-catheter shaft shown as length-adjustable portion 106 in FIG. 1A and length-adjustable portion 108 in FIG. 1B. When fully contracted, as shown in FIG. 1A, the length-adjustable catheter 102 has a total length, $TL_s$, 110 and a shorter usable length, $USL_s$, 112. When the length-adjustable portion of the shaft is fully extended, as shown in FIG. 1B, the length-adjustable catheter has a total length, $TL_l$, 114 and a shorter usable length, $USL_l$, 116. As is readily apparent by comparing FIG. 1A and FIG. 1B, $TL_l$ is greater than $TL_s$ and $USL_l$ is greater than $USL_s$. The difference in length between the contracted configuration 102 and the extended configuration 104 can be seen, by comparing FIGS. 1A and 1B, to be equal to the difference between the extended length L2 (120 in FIG. 1B) of the variable-length portion of the shaft and the length L1 (122 in FIG. 1A) of the contracted variable-length portion of the shaft. This difference, L2−L1, is shown in FIG. 1B as a portion 124 of the extended variable-length portion of the shaft 108 not overlapped by the length of the contracted variable-length portion of the shaft 122 when the two adjustable-catheter configurations 102 and 104 are parallel and aligned. Thus, both the usable length and total length of the length-adjustable angioplasty balloon catheter can be adjusted over a variable-length adjustment range of L2-L1. Both the fully contracted length L1 and the fully extended length L2 of the variable-length portion of the length-adjustable-catheter shaft (106 and 108 in FIGS. 1A-B) may differ in different implementations. As is discussed with reference to subsequent figures, the variable-length portion of the length-adjustable catheter may have different sizes, configurations, shapes, and constructions in different implementations.

The various components and features of the length-adjustable angioplasty balloon catheter are next described with reference to FIG. 1A. The length-adjustable catheter includes a manifold 130 with two ports: (1) an inflation port 132; and (2) a guide-wire port 134. The manifold is mounted over a first end of a catheter shaft 136. In the implementation shown in FIG. 1A, the catheter shaft 136 includes two internal hollow bores, or lumens: (1) a first inflation lumen connected to the inflation port 132; and (2) a second guide-wire lumen connected to the guide-wire port 134. The guide-wire lumen extends from the guide-wire port 134 to the second end, or tip, 138 of the catheter shaft. The adjustable-length catheter is slidably mounted onto a guide wire and translated in either direction along the guide wire during insertion of a portion of the shaft into a patient's blood vessel. The inflation lumen is connected to the inflation port 132 and extends along the catheter shaft to an inflatable catheter balloon 140. Liquids and/or gases, including contrast-agent and saline formulations, air, and other such gases and/or liquids, are transferred, under positive pressure, from the inflation port 132 through the inflation lumen to the inflatable catheter balloon 140, resulting in inflation of the catheter balloon. The various liquids and/or gases are transferred, under negative pressure, from the inflated catheter balloon 140 back through the inflation lumen and out through the inflation port 132, deflating the catheter balloon. In the implementation shown in FIG. 1A, the inflation lumen lies above the guide-wire lumen. The inflation lumen and guide-wire lumen are completely separate from one another, so that there is no possibility for leakage of the liquids and/or gases transported by the inflation lumen into the guide-wire lumen or for leakage of fluids within the guide-wire lumen into the inflation lumen.

In the implementation shown in FIG. 1A, a portion of the catheter shaft close to the manifold is covered by a kink-protection sleeve 142. The usable length of the length-adjustable catheter, $USL_s$, in the configuration shown in FIG. 1A, extends from the tip of the kink-protection sleeve 144 to the catheter tip 138. In the implementation shown in FIG. 1A, the external surfaces of guide-wire and inflation tubes that form internal guide-wire and inflation lumens, respectively, are exposed and visible in the variable-length portion 106, that are covered by an enclosing tube or sheath 146 and 148 on either side of the variable-length portion 106. It should be noted that these tubes may not necessarily be separately manufactured or formed, but may, instead, be portions of a single molded or extruded double-lumen shaft component. In certain implementations, the two enclosing sheaths 146 and 148 have equal outside diameters, while in other implementations, the outside diameters of the two enclosing sheaths 146 and 148 may differ. The variable-length portion (106 and 108 in FIGS. 1A-B) of the catheter shaft is longitudinally and plastically deformable, having a folding pattern embedded into, or imprinted or molded on, the outer surface to facilitate longitudinal extension and contraction. In the implementation shown in FIG. 1A, the inflation tube is parallel to, and positioned above, the guide-wire tube. In alternative implementations, the two tubes may be coaxial, with the guide-wire tube nested within the larger-diameter inflation tube. In certain implementations, the inflation and guide-wire tubes are continuous, comparably rigid tubes, with the portion of the tubes corresponding to the variable-length portions of the shaft patterned or otherwise modified to provide for longitudinal extension and contraction. In alternative implementations, the inflation tube and guide-wire tube each comprises multiple sections of tubing, with middle tube sections corresponding to the variable-length portions of the inflation tube and guide-wire tube each coupled or affixed, at both ends, to tubes corresponding to the non-variable-portions of the inflation tube and guide-wire tube.

FIGS. 2A-B illustrate a second implementation of the length-adjustable angioplasty balloon catheter. In the implementation shown in FIGS. 2A-B, with a contracted configuration 202 shown in FIG. 2A and an extended configuration 204 shown in FIG. 2B, the catheter shaft 206 and 208 has a variable-length portion 210 and 212, similar to the variable-length portion of the catheter shaft of the implementation shown in FIGS. 1A-B. However, the shaft of the length-adjustable catheter implementation shown in FIGS. 2A-B includes two parallel lumens for only a portion 213 of the catheter shaft, and features a smaller manifold 214 with only a single inflation port 216 rather than the two-port manifold (130, 132, and 134 in FIG. 1A) of the first implementation.

This type of implementation is referred to as a "rapid exchange" or "RX" configuration. In the implementation shown in FIGS. 2A-B, a guide-wire port 218 introduces a guide wire 220 into the dual-lumen portion 213 of the catheter shaft. In the implementation shown in FIGS. 2A-B, the outer diameter of the catheter shaft 213 between the variable-length portion 210 and the inflatable catheter balloon 222 has a larger outer diameter than the portion of the catheter shaft between the variable-length region 210 and the kink-protection sleeve 224. In one implementation, the smaller-diameter portion of the catheter shaft comprises a metal hypotube while the larger-diameter portion of the catheter shaft has a polymeric composition. In this implementation, in the dual-lumen portion of the catheter shaft, the inflation tube and guide-wire tube run parallel to one another, and, in various implementations, may have different relative dispositions. In certain implementations, the variable-length portion 210 of the catheter shaft is a separately formed member that is coupled or attached to additional catheter-shaft components, at both ends. In other implementations, the entire guide-wire lumen is a single tube with modifications to the variable-length portion to render the variable-length portion longitudinally extendable and compressible. In other implementations, the portion of the catheter shaft between the inflatable catheter balloon 222 and the variable-length portion 210 may slide over the variable-length portion 210 and, in additional implementations, over additional portions of the catheter shaft, including the single-port manifold.

Figure 3:
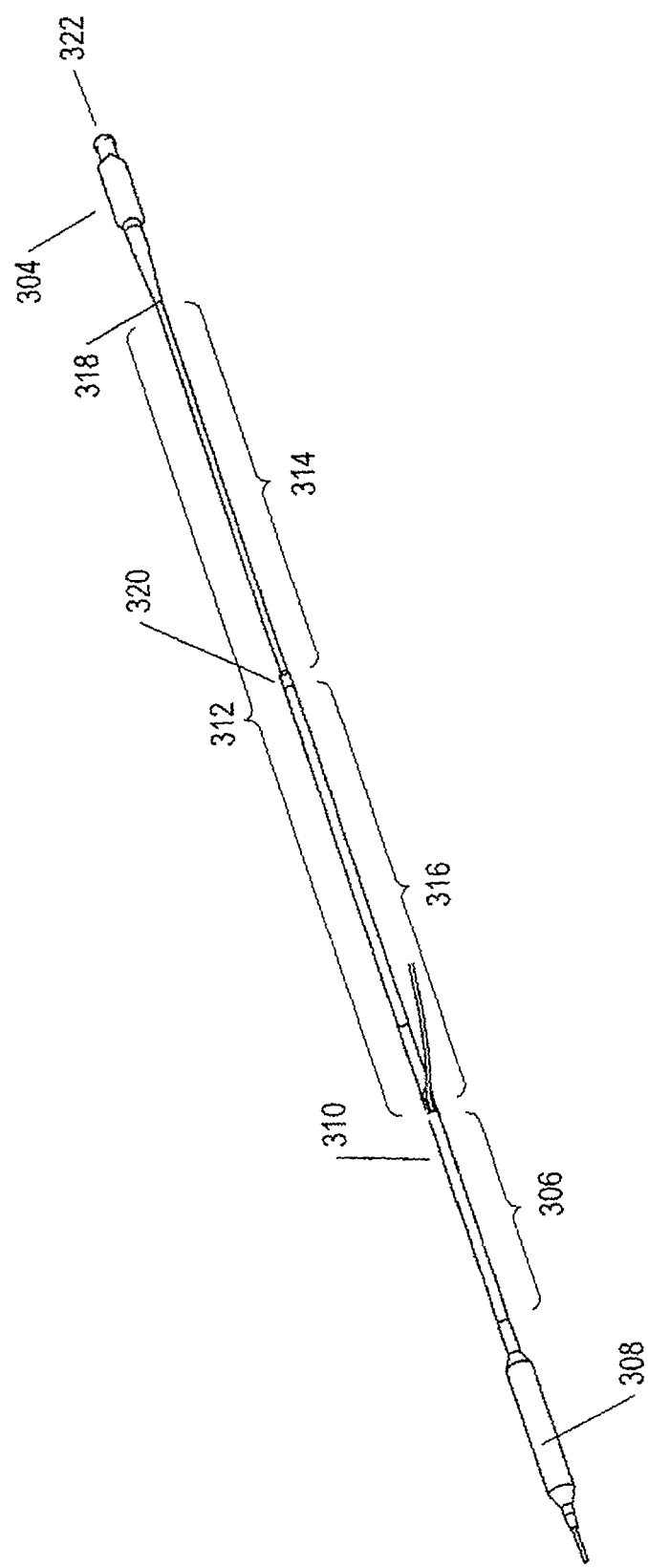
FIG. 3 shows a third implementation of the length-adjustable angioplasty balloon catheter.

FIG. 3 shows a third implementation of the length-adjustable angioplasty balloon catheter. The third implementation is similar to the second implementation, discussed above with reference to FIGS. 2A-B. The third implementation of the length-adjustable angioplasty balloon catheter 302 features the smaller single-port manifold 304 included in the second implementation. The third-implementation also includes a dual-lumen portion of the catheter shaft 306 between the inflatable catheter balloon 308 and the guide-wire port 310. However, unlike the second implementation, the third implementation includes a two-member single-lumen portion of the catheter shaft 312 that includes a smaller-outer-diameter portion 314 and a larger-outer-diameter portion 316. The smaller-outer-diameter portion 314 slides into the larger-outer-diameter portion 316 to provide length adjustability. In FIG. 3, a smaller-outer-diameter portion 314 is shown extended. When contracted, the tip of the kink-protection sleeve 318 is advanced toward a fluid-tight seal 320 as the smaller-outer-diameter portion 314 slides into the larger-outer-diameter portion 316. The fluid-impermeable seal 320 allows the smaller-outer-diameter portion 314 to slide into the larger-outer-diameter portion 316 while maintaining a fluid-impermeable inflation lumen extending from the inflation port 322 to the inflatable balloon catheter 308.

Figure 4:
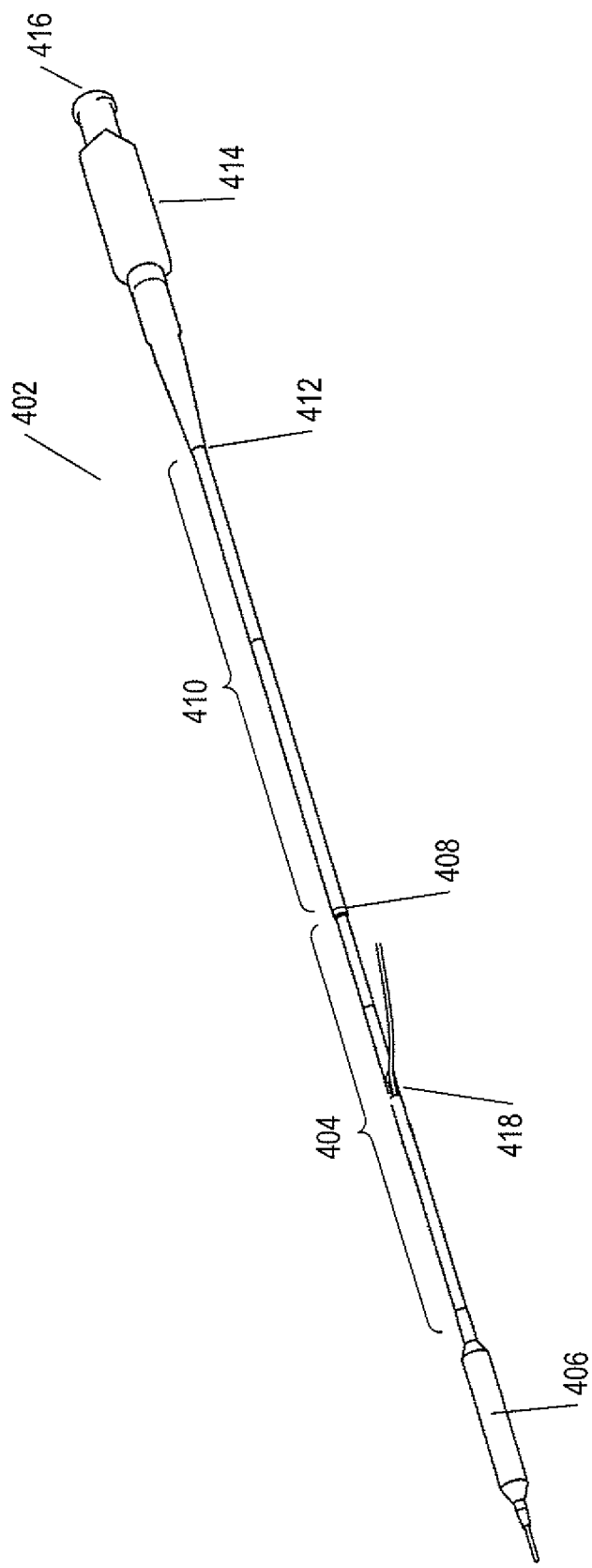
FIG. 4 illustrates a fourth implementation of the length-adjustable angioplasty balloon catheter.

FIG. 4 illustrates a fourth implementation of the length-adjustable angioplasty balloon catheter. A fourth implementation 402 is similar to the third implementation, described above with reference to FIG. 3. However, in the fourth implementation, the portion of the catheter shaft 404 between the inflatable catheter balloon 406 and the fluid-impermeable fitting 408 slides into the portion of the catheter shaft 410 between the fluid-impermeable fitting 408 and the tip of the kink-protection sleeve 412. Thus, the first portion 410 of the catheter shaft has a larger inner diameter than the outer diameter of the second portion 404 of the catheter shaft. As with the implementation shown in FIG. 3, the manifold 414 has a single inflation port 416 and a guide-wire port 418 is located in the second portion 404 of the catheter shaft.

Figure 5:
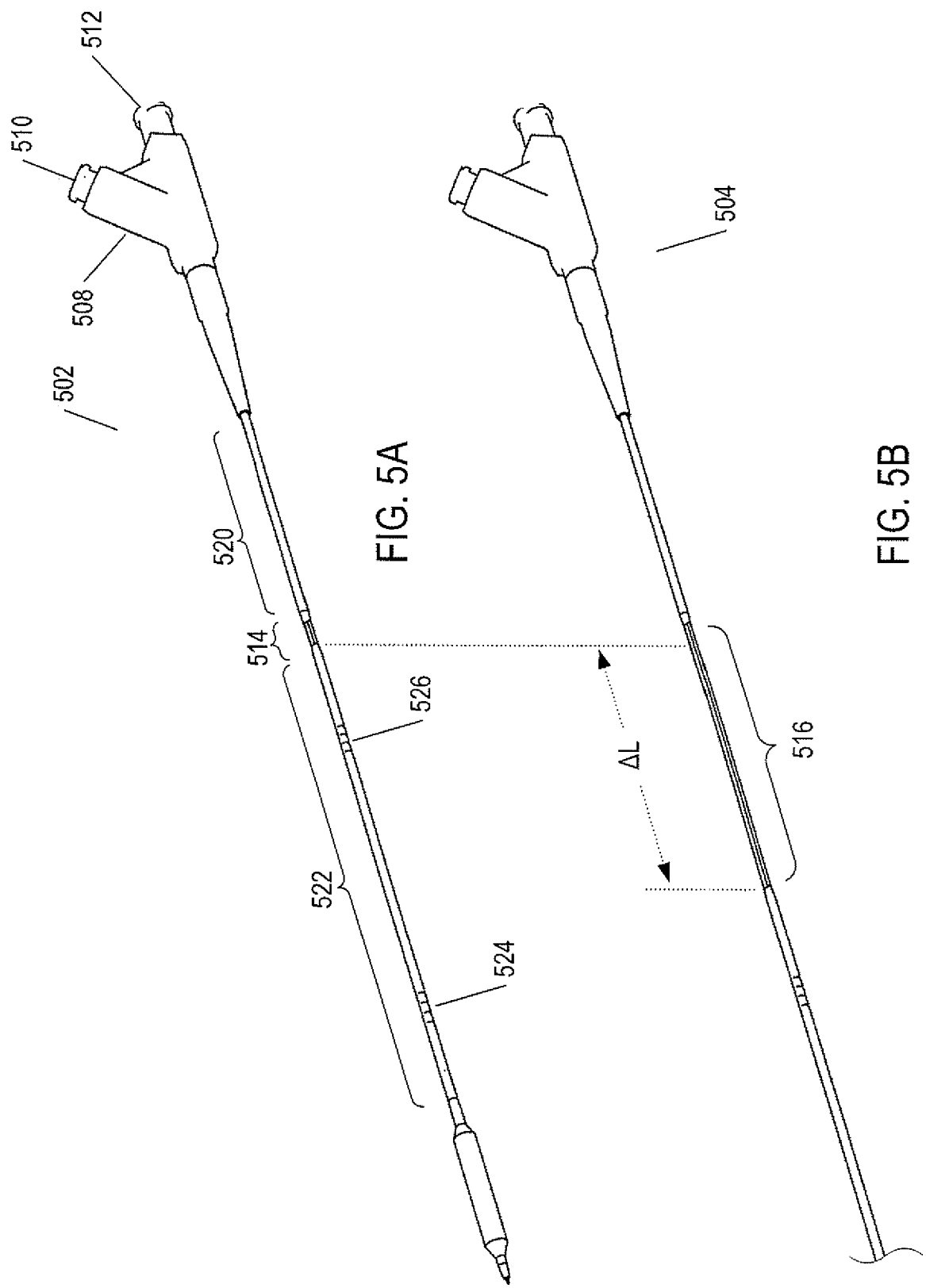
FIGS. 5A-B illustrate a fifth implementation of the length-adjustable angioplasty balloon catheter.

FIGS. 5A-B illustrate a fifth implementation of the length-adjustable angioplasty balloon catheter. A contracted configuration of the length-adjustable catheter is shown in FIG. 5A and an extended configuration of the length-adjustable catheter is shown in FIG. 5B. The fifth implementation bears a similarity to the first implementation, discussed above with reference to FIGS. 1A-B. As in the first implementation, the fifth implementation includes a manifold 508 with an inflation port 510 and a guide-wire port 512. In a fifth implementation, a middle portion of the catheter shaft, 514 in FIG. 5A and 516 in FIG. 5B, comprises a dual-lumen section with an upper inflation lumen and a lower guide-wire lumen, similar to the variable portion of the catheter shaft of the first implementation discussed above with reference to FIGS. 1A-B. However, unlike the first implementation, the middle portion of the catheter shaft 514 and 516 in the fifth implementation is a rigid member over which a first sheath portion 520 and a second sheath portion 522 of the catheter shaft slides. The second sheath portion 522 of the catheter shaft includes two locking engagement zones 524 and 526 that provide fluid-impermeable seals for at least the inflation lumen, in a first set of implementations, and for both the inflation lumen and the guide-wire lumen, in a second set of implementations. These locking engagement zones are discussed further, below, with respect to FIG. 12. The middle section 514 and 516 is, in certain implementations, formed from a metal hypotube. In alternative implementations, the dual-lumen shaft sections may feature coaxial, nested lumens, with the inflation lumen surrounding the guide-wire lumen. The middle section may be fixedly attached to one of the sheath portions 520 and 522, in certain implementations, and is slidably attached to both the first 520 and second 522 sections in alternative implementations.

In all of the above-discussed implementations, the various components of the length-adjustable catheter may be composed of any of many different metals, metal alloys, polymeric materials, and composite materials, including fibers and particulate matter embedded in amorphous, non-crystalline, or semicrystalline micro-crystalline materials. By varying the material compositions of the components, length-adjustable catheters with different operational characteristics are implemented, including differences in rigidity and pliability, differences in the forces needed to extend and contract the variable-length portions of the catheter shaft, differences in surface characteristics with respect to fluids, gases, and biological environments in which the catheter is used, differences in the ability of various imaging technologies to locate and image portions of the catheter when inserted into a patient's blood vessels, and other such characteristics and parameters.

FIGS. 6-11 show a variety of different implementations of dual-lumen and single-lumen shaft-tube engagement configurations and locking mechanisms. These engagement configurations and locking mechanisms may be employed in various of the implementations of the length-adjustable angioplasty balloon catheter, discussed above with reference to FIGS. 1A-5B, as well as in various additional length-adjustable catheter implementations to facilitate engagement and mechanical locking of variable-length portions of the shaft of a length-adjustable catheter with respect to adjacent, enclosed, or enclosing catheter-shaft components.

Figure 6:
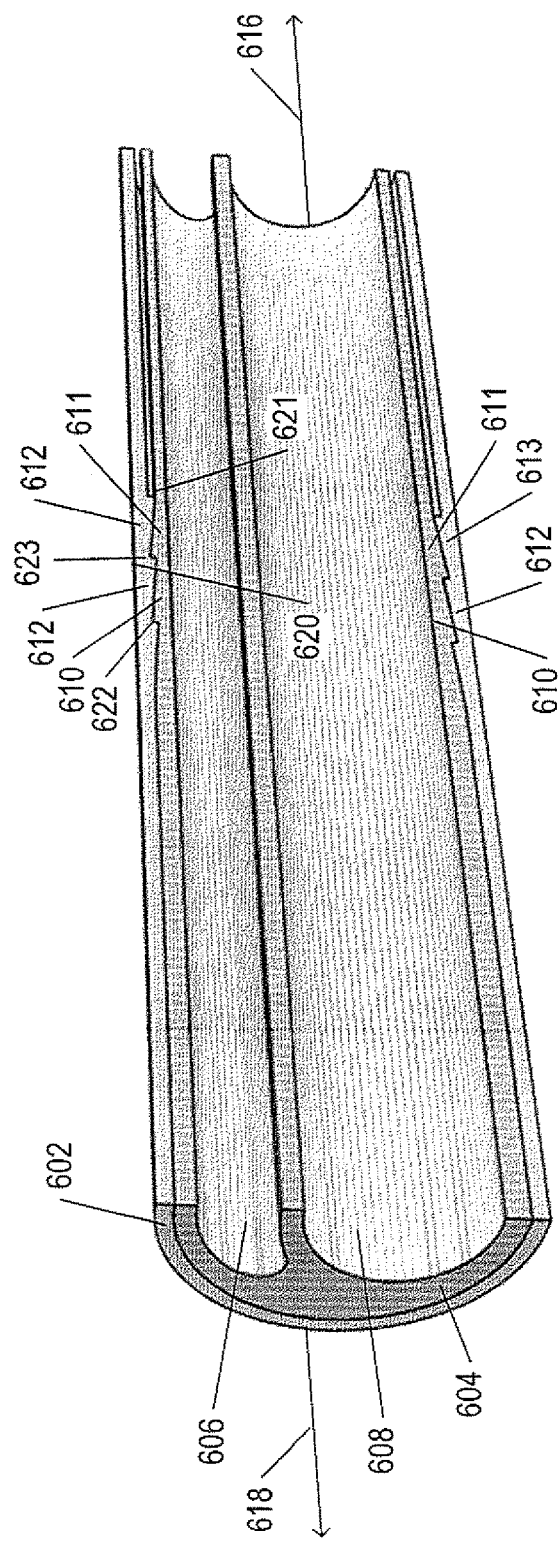

FIG. 6 shows an outer shaft-member tube 602, in cross-section, in which an inner dual-lumen tube 604, also shown in cross-section, is slidably engaged. The inner dual-lumen tube includes an inflation lumen 606 and a wire-guide lumen 608. The inflation lumen and wire-guide lumen 606 and 608 run parallel within the inner tube and are each separately enclosed without fluid communication with one another. In the implementation shown in FIG. 6, the inner tube 604 includes several, annular, ramp-like features 610 and 611 on the outer external surface of the inner tube, shown in cross-section in FIG. 6. Complementary ramp-like features are inscribed within the inner surface of the outer tube 602 to form annular complementary ramp-like features. The annular ramp-like features on the external surface of the inner tube intermesh with the complementary annular ramp-like features inscribed within the inner surface of the outer tube 612 and 613 to lock the position of the inner tube with respect to the outer tube at the position shown in FIG. 6. Application of a longitudinal force to the inner tube 604 in the direction of arrow 616, a longitudinal force on the outer tube in the direction of arrow 618, or opposing longitudinal forces to the inner and outer tubes in the direction of arrows 616 and 618, can overcome forces approximately normal to the ramp-feature surfaces that hold the inner and outer tubes in the position illustrated in FIG. 6, resulting in relative movement of the inner tube with respect to the outer tube in the direction of arrow 616. This movement involves sliding of the ramp-like features on the outer surface of the inner tube against the ramp-like feature surfaces inscribed along the inner surface of the outer tube until the downward-pointing edges of the ramp-like features inscribed within the inner surface of the outer tube 620 and 621 slide past the tops of the ramp-like features 622 and 623 inscribed on the external surface of the inner tube. The tips of the ramp-like features inscribed on the inner surface of the outer tubes 620 and 621 then descend the steep, short faces of the ramp-like features inscribed on the outer surface of the inner tube to again lock into a stable position that represents an advancement of the inner tube in a direction of arrow 616 by a distance corresponding to one ramp-like feature with respect to the outer tube. Movement of the inner tube with respect to the outer tube in a direction opposite from arrow 616 is prevented by the steep, tooth-like notches of the complementary ramp-like features. When the inner tube is translated in the direction of arrow 616 with respect to the outer tube, sliding of the surfaces of the ramp-like features followed by the steep descent of the tips 620 and 621 of the ramp-like features inscribed in the inner surface of the outer tube to a next, locked position provide a haptic, tactile, or sensory signal to a treatment provider who is adjusting the length of a length-adjustable catheter. The dimensions of the complementary ramp-like features, as well as the dimensions of the inner and outer tubes and the inflation lumen and guide-wire lumens within the inner tube may all be varied to generate a variety of related implementations having different operation characteristics, including different incremental translations between locking positions, different amounts of forces needed to be applied in order to move the inner tube with respect to the outer tube, and other such operational characteristics. The inner and outer tubes may comprise any of a variety of different types of polymeric, metal, metal alloy, and other materials, which also impart variations in the operational characteristics of the length-adjustable catheter in which the engagement configuration and locking mechanism is employed.

Figure 7:
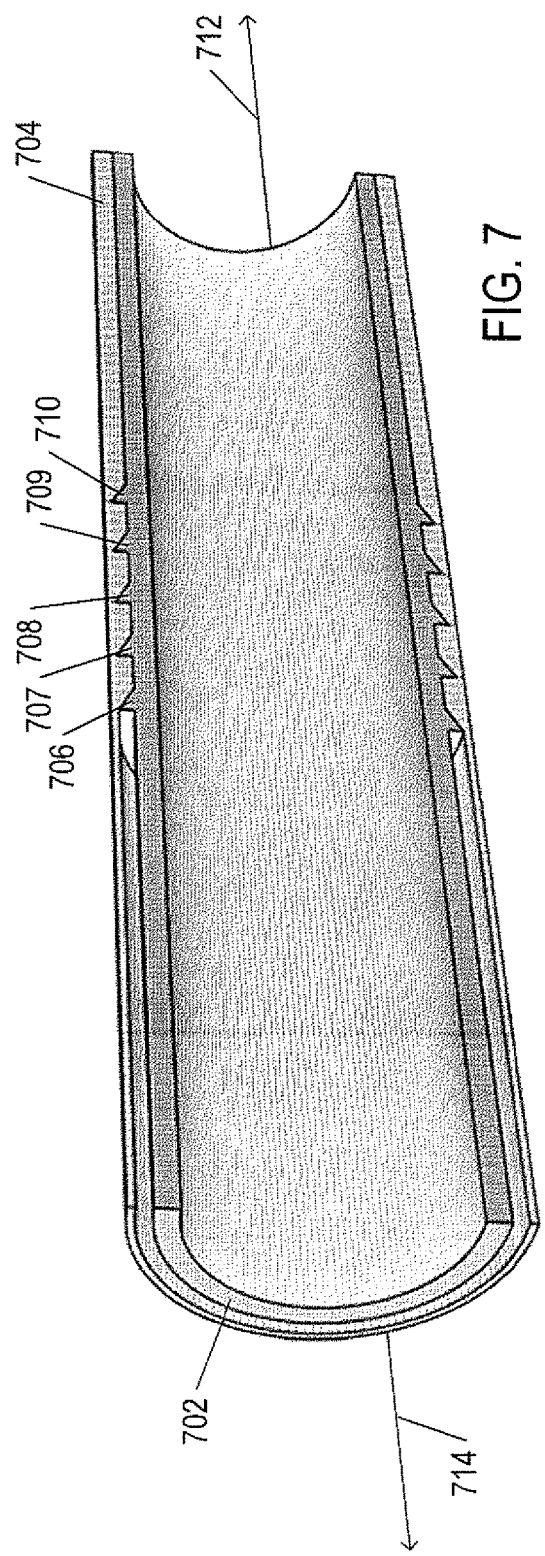

FIG. 7 illustrates another type of engagement configuration and locking mechanism used in various implementations of the above-described length-adjustable angioplasty balloon catheter. In FIG. 7, an inner, single-lumen tube 702, shown in cross-section, resides within a larger-diameter, outer catheter-shaft tube 704. Sawtooth-like features 706-710 are circularly disposed around the outer surface of the inner tube. As with the complementary ramp-like features discussed above with reference to FIG. 6, the sawtooth-like features on the outer surface of the inner tube, shown in cross-section in FIG. 7, fit within complementarily shaped grooves inscribed within the inner surface of the outer sheath or tube 704. As in the case in the implementation shown in FIG. 6, a longitudinal force applied in the direction of arrow 712 on the inner tube, in the direction of arrow 714 on the outer tube, or two opposing forces applied together to the inner and outer tubes in the directions 712 and 714, respectively, allow the inner tube to advance in the direction of arrow 712 with respect to the outer tube by an interval equal to the spacing between the sawtooth-like features. As in the implementation discussed above with reference to FIG. 6, the relative movement of the inner tube with respect to the outer tube provides haptic, tactile, or sensory feedback to a treatment provider extending or contracting a length-adjustable catheter. As with the implementation discussed above with reference to FIG. 6, the engagement configuration and locking mechanism illustrated in FIG. 7 allows for movement of the inner tube in the direction of arrow 712 with respect to the outer tube, but prevents movement of the inner tube with respect to the outer tube in the opposite direction. As with the implementation discussed above with reference to FIG. 6, and subsequent implementations discussed below with reference to FIGS. 8-11, the operational characteristics of the engagement configuration and locking mechanism illustrated in FIG. 7 may vary as the material composition, dimensions, inter-feature spacings, and other parameters of the engagement configuration and locking mechanism are varied.

FIGS. 8-9 illustrate alternative engagement configurations and locking mechanisms, similar to those discussed above with reference to FIG. 7. As shown in FIG. 8, circular, rib-like features 802-806, shown in cross-section in FIG. 8, are formed on the external surface of the inner tube 808 and fit into complementary circular, rounded well-like features inscribed on the inner surface of an outer tube 810. As with the engagement configuration and locking mechanism discussed above with reference to FIG. 7, the complementary features hold the inner tube at a stable position with respect to the outer tube. As shown in FIG. 9, symmetrical, wedge-shaped annular features 902-906 are formed in the outer surface of the inner tube 908 complementary to V-shaped annular depressions on the inner surface of an outer tube 910. In certain implementations of the engagement configuration and locking mechanism shown in FIGS. 8 and 9, the locking mechanisms provide advancement of the inner tube with respect to the outer tube in both longitudinal directions. In other implementations, a stop feature may be included at one extremity of the annular features on the external surface of the inner tube or the annular features on the inner surface of the outer tube, or both, to prevent advancement in one direction past the stop position but allow advancement in the other direction.

Figure 10:
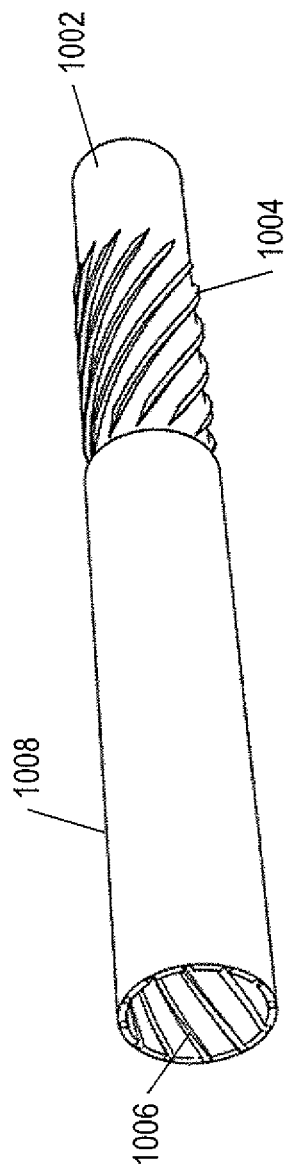

FIG. 10 illustrates an additional implementation of an engagement configuration and locking mechanism. In this implementation, the external surface of an inner tube 1002 includes helical thread-like features, including helical thread-like feature 1004, that are complementary to helical depressions or wells, such as helical depression 1006, in the inner surface of an outer tube 1008. The helical threads and/or notches may span only a portion of the outer surface of the inner tube and inner surface of the outer tube, providing for relative motion of the inner tube with respect to the outer tube over only that distance along the lengths of the two tubes. Alternatively, annular non-notched sections of the inner surface of the outer tube, positioned at intervals along the length of the outer tube, can provide regularly spaced stopping points, as in the implementations discussed above with reference to FIGS. 6-9, to allow the inner tube to be advanced with respect to the outer tube by fixed increments. In additional implementations, the inner surface of the outer tube may have raised threads complementary to wells or notches in the external surface of the inner tube.

Figure 11:
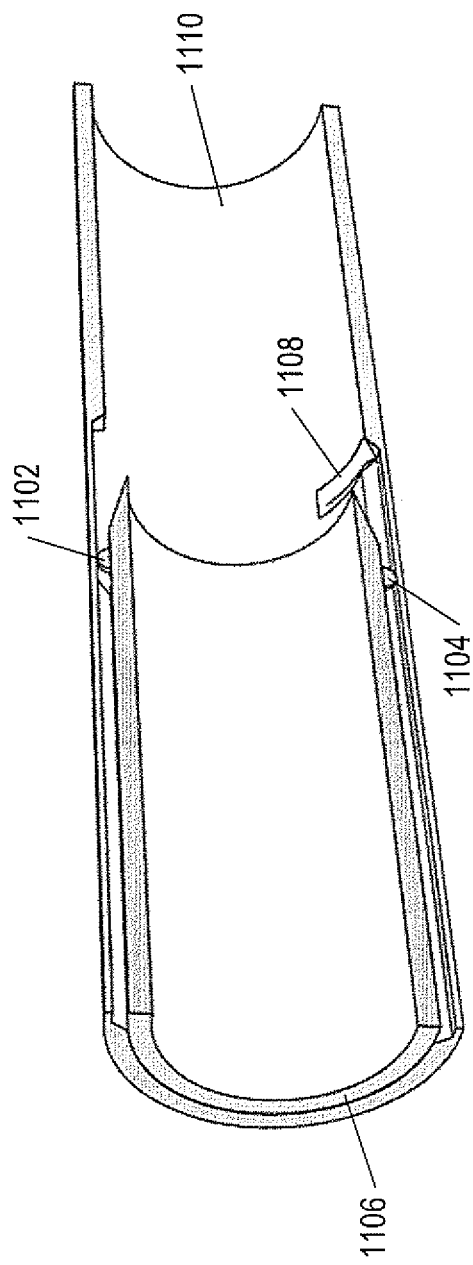

FIG. 11 provides yet an additional implementation of an engagement configuration and locking mechanism. As shown in FIG. 11, rounded or wedge-shaped pins 1102 and 1104 formed on the outer surface of the inner tube 1106 are complementary to curved wells or notches 1108 on the inner surface of the outer tube 1110. The pins 1102 and 1104 can be rotated, by rotation of the inner tube relative to the outer tube, to engage and disengage from the notches 1108. In this implementation, rotation of the inner tube to disengage the pins from the notches followed by application of a longitudinal force to either or both the inner and outer tubes allows for movement of the inner tube with respect to the outer tube in the longitudinal direction. Following translation of the inner tube with respect to the outer tube, the inner tube can be again rotated in order to engage the pins in a next slot within the inner surface of the outer tube to lock the position of the inner tube with respect to the outer tube.

Figure 12:
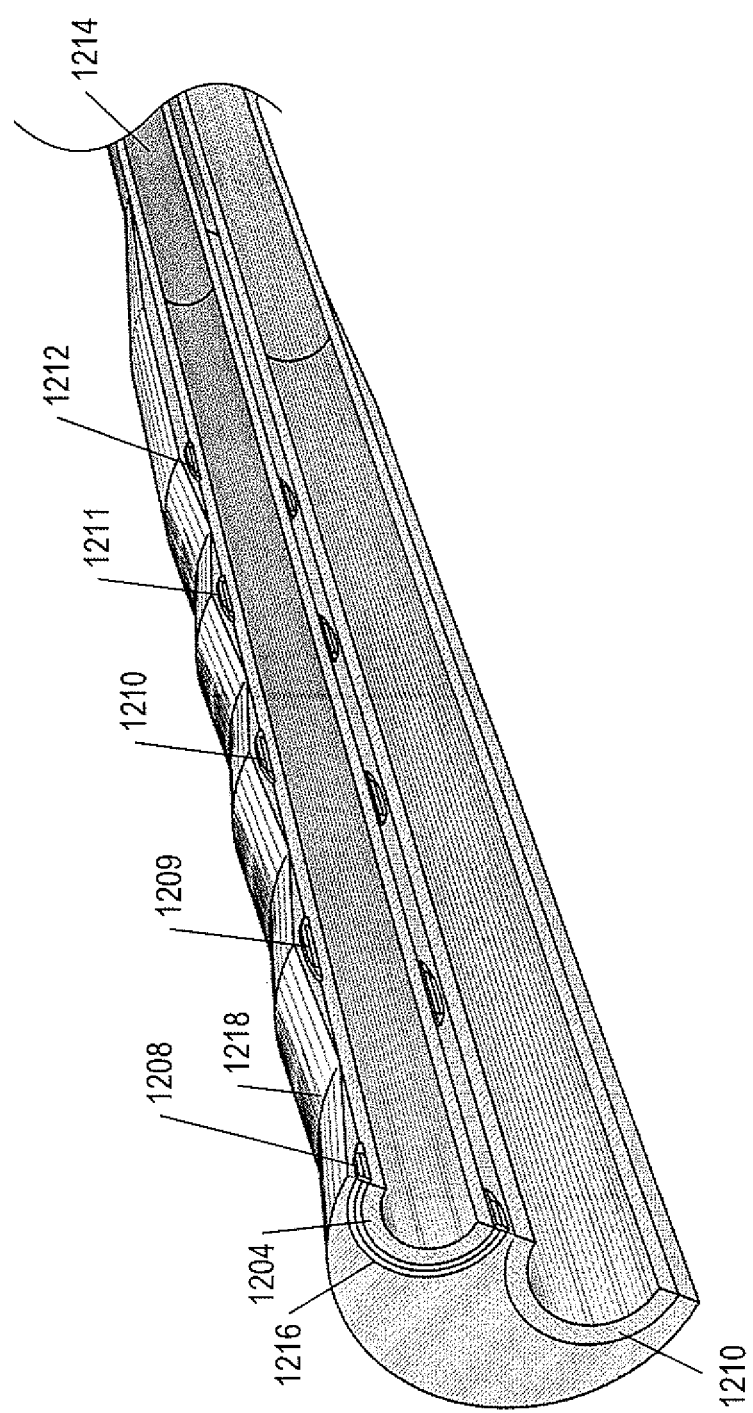
FIG. 12 illustrates an engagement configuration and locking mechanism that, as one example, may be employed in the length-adjustable angioplasty balloon catheter implementation shown in FIGS. 5A-B.

FIG. 12 illustrates an engagement configuration and locking mechanism that, as one example, may be employed in the length-adjustable angioplasty balloon catheter implementation shown in FIGS. 5A-B. In this implementation, a double-lumen pair of inner tubes 1202 and 1204 are enclosed within an outer sheath or tube 1206. Annular radio-opaque marker rings 1208-1212 are positioned at regular intervals along the outer surface of the inflation lumen 1214 of the double-lumen inner tube. The radio-opaque marker rings are each encapsulated within an elastomeric sealant ring, such as the elastomeric sealant ring 1216 covering annular radio-opaque marker 1208. The elastomeric sealant rings and covered radio-opaque marker rings together form annular protrusions, or bumps, at regular intervals on the external surface of the inflation lumen 1214. These annular bumps are complementary to rounded wells within the inner surface of the outer sheath 1206. The outer sheath has a series of annular grooves, such as annular groove 1218, patterned along the external surface of the sheath to facilitate manipulation by a treatment provider. The inner double-lumen tube can be incrementally translated with respect to the outer sheath 1206 by incremental lengths equal to the distance between the elastomeric annular sealant rings and complementary annular wells along the outer surface of the inner tube and interior surface of the outer sheath.

Figure 13:
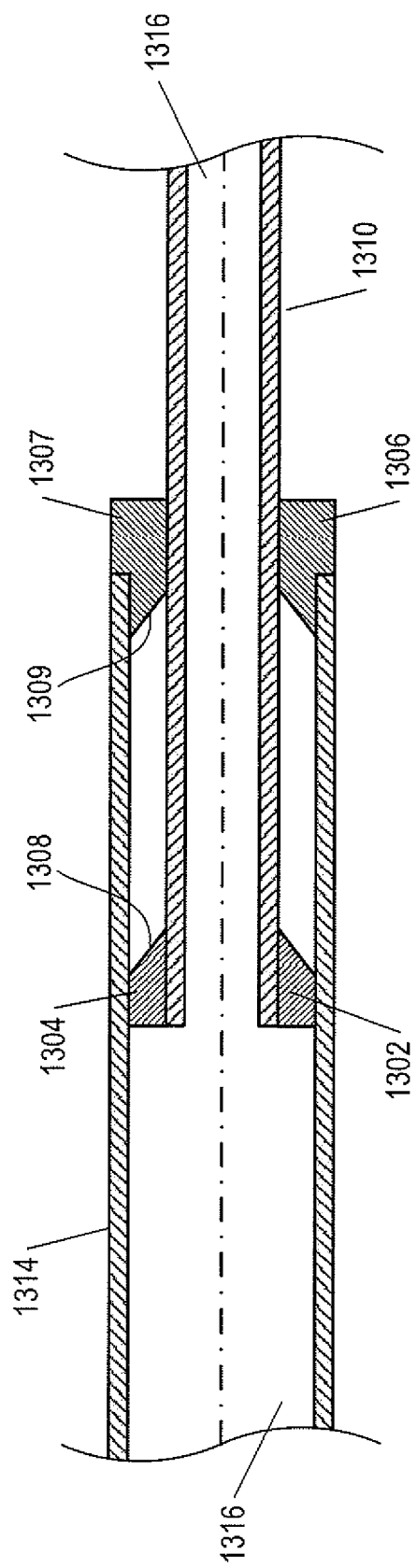
FIG. 13 shows, in cross-section, a fitting that provides a fluid-impermeable slidable seal to facilitate sliding of a smaller-diameter portion of a length-adjustable catheter shaft within a larger-diameter portion of the catheter shaft.

The length-adjustable angioplasty balloon catheter implementations discussed above with reference to FIGS. 3-4 include a slidable length adjustment in which a larger-diameter portion of the catheter shaft slides over a smaller-diameter portion of the catheter shaft. FIG. 13 shows, in cross-section, a fitting that provides a fluid-impermeable slidable seal to facilitate sliding of a smaller-diameter portion of a length-adjustable catheter shaft within a larger-diameter portion of the catheter shaft. As shown in FIG. 13, the fitting includes an inner sealing annulus 1302 and 1304, shown in cross-section in FIG. 13, and a complementary outer sealing ring 1306 and 1307. The sealing rings have complementary ramp-like surfaces, including ramp-like surfaces 1308 and 1309, so that the two sealing rings together form a stop when the smaller-diameter portion of the catheter shaft 1310 is translated in the direction of arrow 1312 with respect to the larger-diameter portion of the catheter shaft 1314 and reaches a point where the ramp-like surface of the inner sealing ring 1308 meets the complementary ramp-like surface 1309 of the outer sealing ring 1307. The inner and outer sealing rings together provide a fluid-impermeable fitting that slidably connects the smaller-diameter portion of the catheter shaft 1310 with the larger-diameter portion of the catheter shaft 1314 to provide a single, continuous lumen 1316 that is length adjustable.

Figure 14:
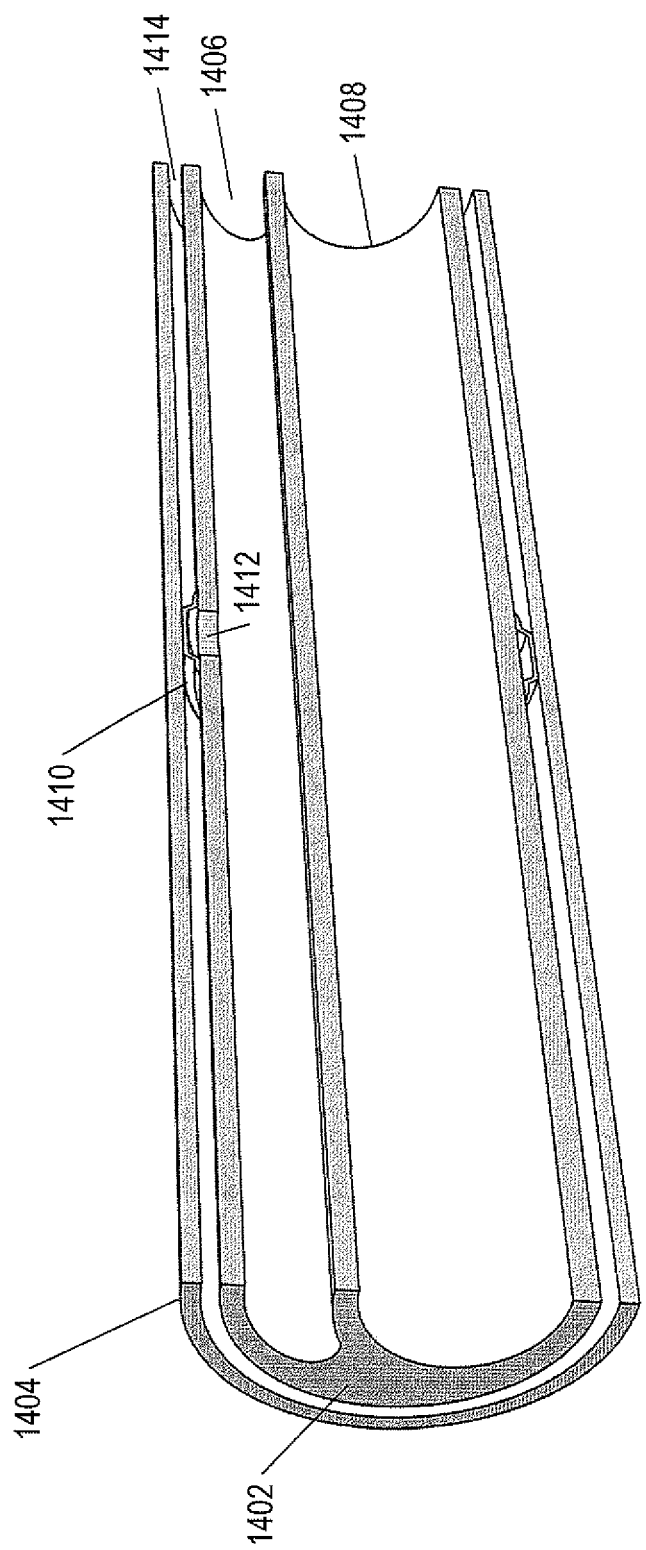
FIG. 14 shows an additional engagement configuration and locking mechanism.

FIG. 14 shows an additional engagement configuration and locking mechanism. As shown in FIG. 14, a double-lumen inner tube 1402 is slidably mounted within an outer, larger-diameter tube 1404. The double-lumen tube includes an inflation lumen 1406 and a guide-wire lumen 1408. An annular elastomeric membrane 1410 is affixed to the outer surface of the inner tube 1402 above an inflation port 1412. The inflation port, when pressure within the inflation lumen 1406 exceeds a first threshold pressure, expands into the elastomeric membrane 1410 to mechanically engage and lock the position of the inner tube with respect to the outer tube. In addition, the pressure-induced expansion of the elastomeric membrane 1410 creates a fluid-impermeable seal that seals the narrow lumen between the outer tube 1404 and inner tube 1402. The first pressure threshold is significantly less than a second pressure threshold, above which the balloon catheter of a length-adjustable angioplasty balloon catheter is inflated via pressure within the inflation lumen 1406.

Figure 15:
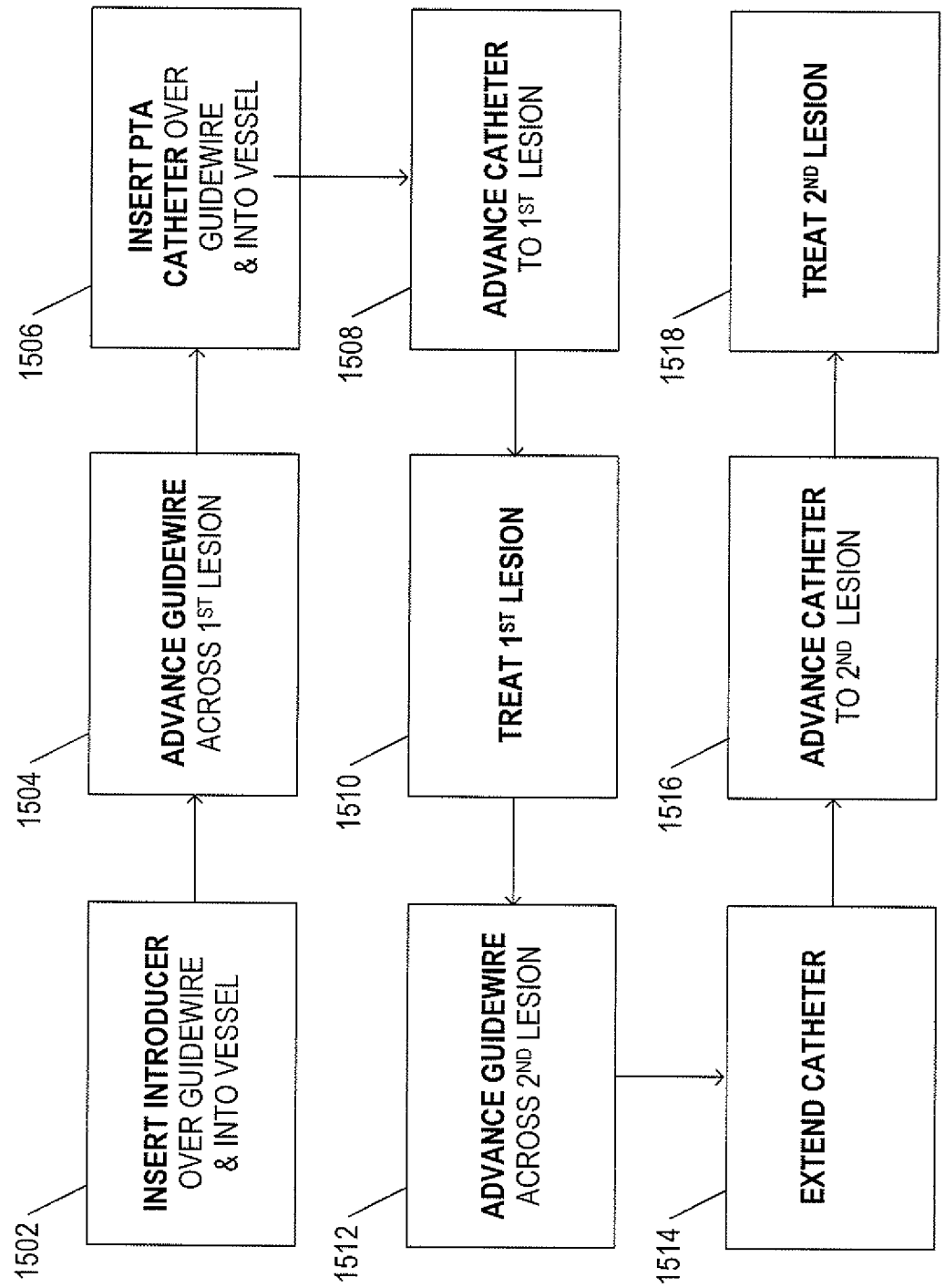
FIG. 15 shows a series of steps carried out by a treatment provider, using a length-adjustable angioplasty balloon catheter, to treat multiple blockages or lesions within a patient's blood vessel.

FIG. 15 shows a series of steps carried out by a treatment provider, using a length-adjustable angioplasty balloon catheter, to treat multiple blockages or lesions within a patient's blood vessel. In step 1502, the treatment provider inserts an introducer sheath into the patient's blood vessel under hemostatic conditions to provide access to the blood vessel for catheters and other treatment devices. In step 1504, the treatment provider advances a guide wire through the introducer sheath into the patient's blood vessel and positions the end of the guide wire within a first target treatment area. In step 1506, the treatment provider inserts a length-adjustable angioplasty balloon catheter through the introducer sheath and over the guide wire and, in step 1508, advances the length-adjustable catheter along the guide wire to a position at which the length-adjustable catheter can be manipulated to treat or ameliorate the blockage or lesion and restore luminal patency. As the result of treatment at the first target site, additional lesions further down the patient's blood vessel may become observable. In step 1512, the treatment provider advances the guide wire to a next target treatment site. In step 1514, the treatment provider extends the length-adjustable catheter and, in step 1516, advances the end of the length-adjustable catheter to the second target site. In step 1518, the catheter is manipulated in order to remove or ameliorate a second blockage or lesion. The steps shown in FIG. 15 are an example of the use of a length-adjustable catheter. Other examples include extending a length-adjustable catheter or contracting a length-adjustable catheter, following initial positioning, in order to correct a discrepancy in the initial positioning of the catheter. Additional examples include treatment of more than two lesions or blockages.

Figure 16:
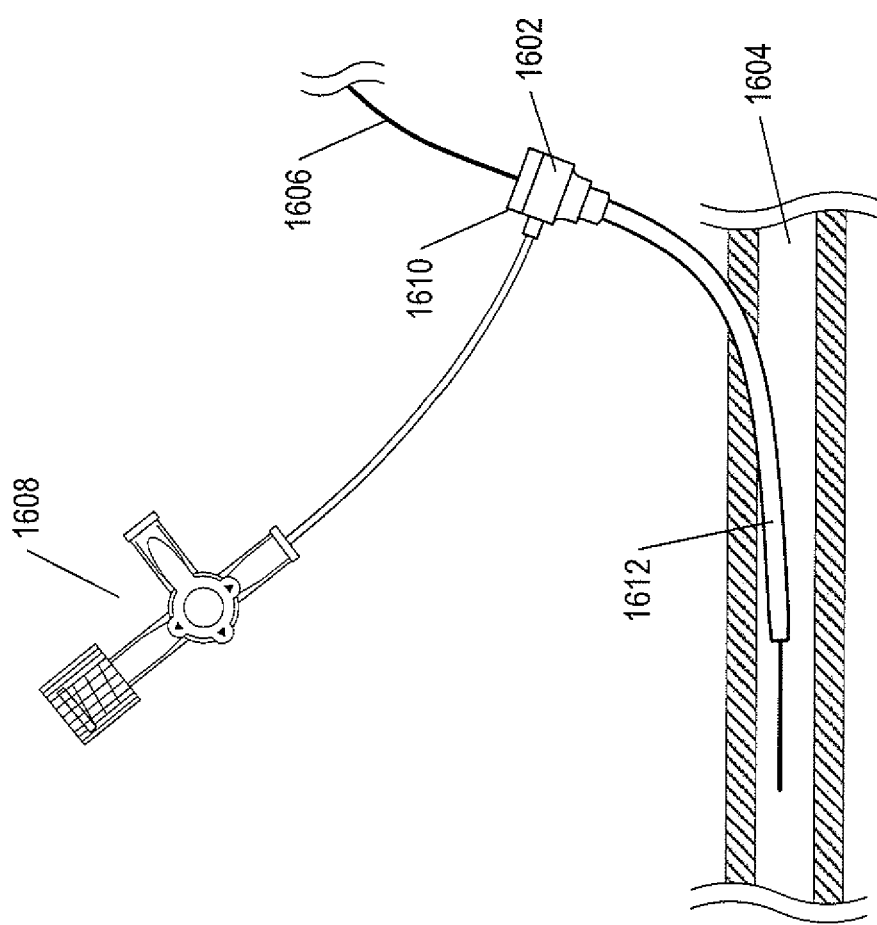
FIG. 16 illustrates insertion of an introducer sheath into a patient's blood vessel followed by insertion of a guide wire.

FIGS. 16-20 provide additional illustration of selected steps discussed above with reference to FIG. 15. FIG. 16 illustrates insertion of an introducer sheath into a patient's blood vessel followed by insertion of a guide wire. The introducer 1602 is inserted through a puncture site in the wall of the patient's blood vessel 1604. The introducer, in the example shown in FIG. 16, includes a three-way stopcock valve 1608 for delivery of fluids into the patient's blood vessel and a hemostasis value 1610 for prevention of bleeding. The introducer sheath 1612 provides for insertion and guidance of guide wires and subsequent insertion of catheters over the guide wires under hemostatic conditions.

Figure 17:
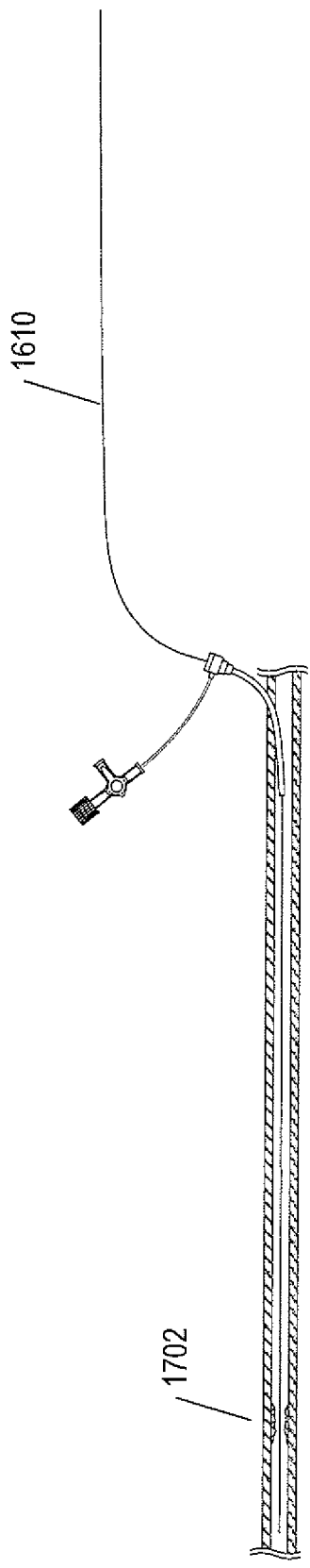
FIG. 17 illustrates advancement of a guide wire into a patient's blood vessel across a target treatment site.

FIG. 17 illustrates advancement of a guide wire into a patient's blood vessel across a target treatment site. The tip of the guide wire 1610 has been advanced, relative to the initial position shown in FIG. 16, past a first treatment site 1702. Advancement of the guide wire may be monitored by radiographic means or other medical-imaging technology.

Figure 18:
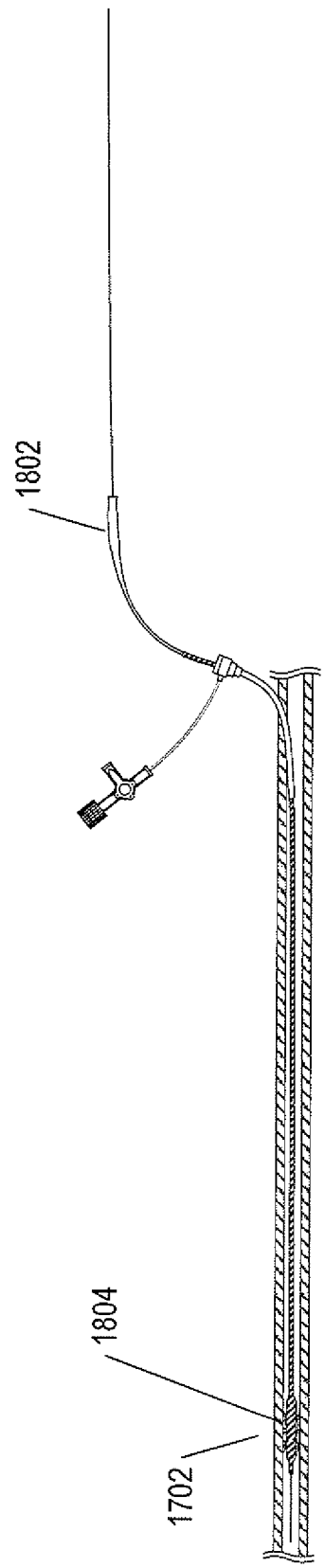
FIG. 18 illustrates introduction of a length-adjustable catheter over a guide wire through an introducer into a patient's blood vessel.

FIG. 18 illustrates introduction of a length-adjustable catheter over a guide wire through an introducer into a patient's blood vessel. The length-adjustable catheter 1802 has been positioned so that the catheter balloon 1804 straddles the treatment target site 1702. The catheter balloon can be subsequently inflated, via application of fluid under pressure through the inflation lumen, in order to ameliorate the blockage or lesion at the treatment sites. Alternatively, the length-adjustable catheter can be manipulated, in other ways, to ameliorate or dislodge an obstruction or blockage.

Figure 19:
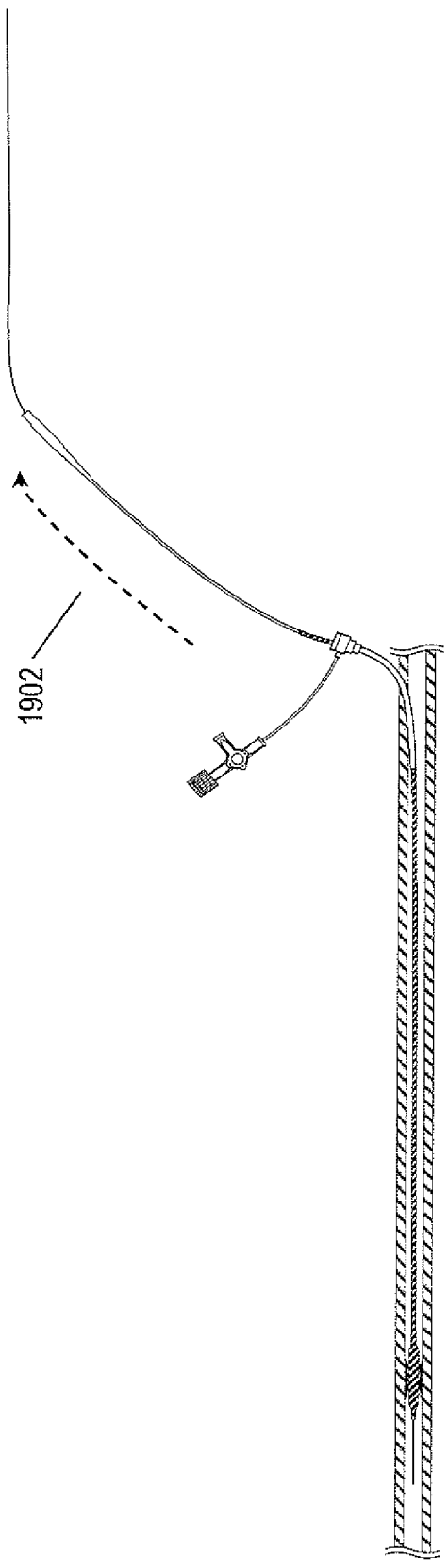
FIG. 19 illustrates length-adjustable catheter extension.

FIG. 19 illustrates length-adjustable catheter extension. As indicated by dashed arrow 1902, a treatment provider manipulates the catheter shaft that is exposed above the introducer in order to lengthen the catheter, with the lengthening occurring in the portion of the catheter shaft external to the introducer and patient's blood vessel. Various different techniques may be used for catheter extension, depending on the types of variable-length portions of the catheter shaft and the types of engagement configurations and locking mechanisms included in the catheter.

Figure 20:
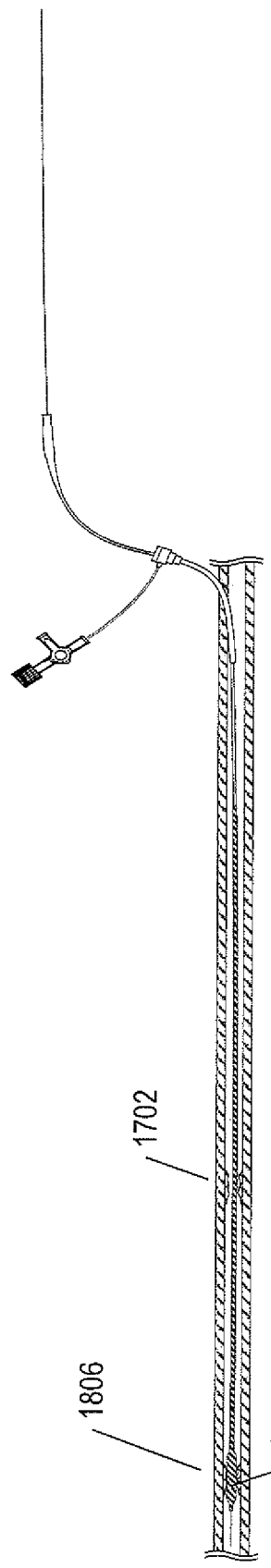
FIG. 20 illustrates advancement of an extended length-adjustable catheter to a second target area.

FIG. 20 illustrates advancement of an extended length-adjustable catheter to a second target area. The extended length-adjustable catheter is advanced along the guide wire past the first target site so that the catheter balloon 1804 is positioned to straddle a second treatment site 1806.

Although the present invention has been described in terms of particular embodiments, it is not intended that the invention be limited to these embodiments. Modifications within the spirit of the invention will be apparent to those skilled in the art. For example, as mentioned above, there are many different possible implementations of a length-adjustable catheter. In general, the length of the catheter shaft can be altered, before and/or during a treatment procedure, in order to provide access to multiple positions within a blood vessel. In either the dual-lumen or single-lumen implementations, the inflation lumen remains fluid impermeable before, during, and after extension or contraction of the length-adjustable catheter. Furthermore, the catheter retains a proper balance between rigidity and flexibility, over the adjustable length range, for carrying out intended medical procedures. The various components of a length-adjustable catheter can be fabricated from a variety of different materials, including metals, metal alloys, polymeric materials, and other suitable material compositions. Length-adjustable catheters can be designed and manufactured to have a variety of different length ranges, diameters, internal lumen volumes, extension and contraction forces, surface characteristics, and other such characteristics. In many implementations, the length-adjustable catheters include engagement-configuration and locking mechanisms so that the medical practitioner can sense precise amounts of length adjustment and can lock the length-adjustable components of the catheter sheath at a fixed, intended length. In addition, various features may be provided at regular intervals along the catheter sheath to aid in catheter positioning, position sensing, and length adjustment, including optically detectable features and features detectable by various medical-imaging technologies.

It is appreciated that the previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

The invention claimed is:

1. A length-adjustable catheter comprising:
   a guide-wire input port;
   an inflation port;
   a shaft, the length of which can be varied over a length-adjustment range, that further comprises
      a guide-wire lumen that extends from the guide-wire input port, through a portion of the shaft, to an opening at a tip of the catheter;
      a length-adjustable inflation lumen that extends from the inflation port, through the shaft, to an inflatable length-adjustable-catheter component and
      a mechanical position-maintaining feature that maintains the shaft at a constant length prior to and following length adjustment, the mechanical position-maintaining feature comprising
         a set of radio-opaque marker rings positioned at regular intervals along an outer surface of a first tube, each radio-opaque marker ring encapsulated within an elastomeric sealant ring,
         a set of rounded wells within an inner surface of a second enclosing tube, each rounded well complementary in shape to each of the radio-opaque marker rings, into one or more of which one or more of the radio-opaque marker rings fits in order to impede sliding of the first tube relative to the second tube, and a set of annular grooves patterned along an external surface of the second enclosing tube to facilitate manual translation of the first tube relative to the second tube.

* * * * *